(12) United States Patent
Naidu

(10) Patent No.: US 12,097,344 B2
(45) Date of Patent: Sep. 24, 2024

(54) INTRODUCER NEEDLE HAVING A BUMP AND RELATED SYSTEMS AND METHODS

(71) Applicant: Becton, Dickinson and Company, Franklin Lakes, NJ (US)

(72) Inventor: Jithendra Kumar Sathyanarayana Naidu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 144 days.

(21) Appl. No.: 17/508,105

(22) Filed: Oct. 22, 2021

(65) Prior Publication Data

US 2022/0152359 A1    May 19, 2022

Related U.S. Application Data

(60) Provisional application No. 63/114,276, filed on Nov. 16, 2020.

(51) Int. Cl.
*A61M 25/06* (2006.01)
*A61M 39/10* (2006.01)

(52) U.S. Cl.
CPC .... *A61M 25/0606* (2013.01); *A61M 25/0637* (2013.01); *A61M 39/10* (2013.01); *A61M 2039/1072* (2013.01); *A61M 2039/1077* (2013.01)

(58) Field of Classification Search
CPC ...... A61M 2039/1072; A61M 25/0606; A61M 25/0637; A61M 25/065; A61M 2210/12; A61M 5/46; A61M 2205/582
See application file for complete search history.

(56) References Cited

U.S. PATENT DOCUMENTS

| | | | |
|---|---|---|---|
| 5,215,537 A * | 6/1993 | Lynn | A61M 39/045 215/249 |
| 5,743,882 A | 4/1998 | Luther | |
| 2009/0131870 A1* | 5/2009 | Fiser | A61M 25/0618 604/162 |

(Continued)

FOREIGN PATENT DOCUMENTS

| | | |
|---|---|---|
| EP | 1785159 | 5/2007 |
| WO | 2007/050788 | 5/2007 |

(Continued)

*Primary Examiner* — Nathan R Price
*Assistant Examiner* — Haden Matthew Ritchie
(74) *Attorney, Agent, or Firm* — Kirton McConkie; Whitney Blair; Kevin Stinger

(57) ABSTRACT

A catheter system may include a catheter adapter, which may include a distal end, a proximal end, and a lumen extending through the distal end of the catheter adapter and the proximal end of the catheter adapter. The catheter system may include a septum assembly disposed within the lumen of the catheter adapter. The catheter system may include a catheter extending from the distal end of the catheter adapter. The catheter system may include an introducer needle, which may include a proximal end, a sharp distal tip, and a bump disposed between the proximal end and the sharp distal tip. The proximal end of the introducer needle may be secured within a needle hub of the catheter system. In response to the bump contacting the septum assembly, the sharp distal tip of the introducer needle is disposed distal to a distal end of the catheter.

18 Claims, 7 Drawing Sheets

(56) References Cited

U.S. PATENT DOCUMENTS

2011/0224617 A1    9/2011  Miner
2017/0120010 A1*   5/2017  Burkholz ............ A61M 5/1626
2020/0353222 A1   11/2020  Jaquez

FOREIGN PATENT DOCUMENTS

WO      2011097639 A2    8/2011
WO      2021/078525      4/2021
WO      2021078535 A1    4/2021

* cited by examiner

INTRODUCER NEEDLE HAVING A BUMP AND RELATED SYSTEMS AND METHODS

RELATED APPLICATIONS

This application claims benefit of U.S. Provisional Patent Application No. 63/114,276, filed on Nov. 16, 2020, entitled INTRODUCER NEEDLE HAVING A BUMP AND RELATED SYSTEMS AND METHODS, which is incorporated herein in its entirety.

BACKGROUND

Catheters are commonly used for a variety of infusion therapies. Catheters may be used for infusing normal saline solution, various medicaments, total parenteral nutrition, or other fluids into a patient. Catheters may also be used to withdraw blood from the patient for diagnostic or other purposes.

A common type of catheter is a peripheral intravenous catheter ("PIVC") that is "over-the-needle." As its name implies, the PIVC that is over-the-needle may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into the vasculature of the patient.

In order to verify proper placement of the introducer needle and/or the PIVC in the blood vessel, a clinician generally confirms that there is "flashback" of blood in a flashback chamber of the catheter assembly. Once placement of the needle has been confirmed, the clinician may remove the introducer needle, leaving the PIVC in place for future fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices, systems, and methods. In particular, the present disclosure relates to an introducer needle that includes a bump, as well as related systems and methods. In some embodiments, a catheter system may include a catheter adapter, which may include a distal end, a proximal end, and a lumen extending through the distal end of the catheter adapter and the proximal end of the catheter adapter. In some embodiments, the catheter system may include a septum assembly disposed within the lumen of the catheter adapter. In some embodiments, the septum assembly may include a septum and/or a septum canister.

In some embodiments, the catheter system may include a catheter extending from the distal end of the catheter adapter. In some embodiments, the catheter system may include a needle hub coupled to the proximal end of the catheter adapter. In some embodiments, the catheter system may include an introducer needle, which may include a proximal end, a sharp distal tip, and a bump disposed between the proximal end and the sharp distal tip. In some embodiments, the proximal end of the introducer needle is secured within the needle hub. In some embodiments, in response to the bump contacting the septum assembly, the sharp distal tip of the introducer needle is disposed distal to a distal end of the catheter.

In some embodiments, the sharp distal tip of the introducer needle may include a bevel. In some embodiments, a distance between the bump and the septum assembly may be less than or equal to a lie distance between the distal end of the catheter and a proximal end of the bevel of the introducer needle. In some embodiments, the septum assembly may include a distal end, and the bump may be in contact with the distal end of the septum assembly. In some embodiments, the bump may be distal to and spaced apart from the septum assembly. In some embodiments, the bump may be no more than 2 mm from the septum assembly. In some embodiments, the introducer needle may include a notch distal to the bump.

In some embodiments, the catheter assembly may include a wing extending outwardly from the catheter adapter. In some embodiments, the needle assembly may include a paddle hub extending outwardly from the needle hub. In some embodiments, the paddle hub may include a lip configured to abut the wing and prevent proximal movement of the wing with respect to the paddle hub. In some embodiments, the wing may be configured to slide distally with respect to the paddle hub.

In some embodiments, the bump is a first bump, and the introducer needle may include a second bump distal to the first bump. In some embodiments, in response to the second bump contacting the septum assembly, the sharp distal tip of the introducer needle may be disposed distal to the distal end of the catheter. In some embodiments, the sharp distal tip of the introducer needle may include a bevel, and a distance between the second bump and the septum assembly may be less than or equal to a lie distance between the distal end of the catheter and a proximal end of the bevel of the introducer needle.

In some embodiments, the septum assembly may include a distal end. In some embodiments, the first bump may be in contact with the distal end of the septum assembly. In some embodiments, the first bump may be distal to and spaced apart from the septum assembly. In some embodiments, the second bump may be no more than 2 mm from the septum assembly.

In some embodiments, the first bump and/or the second bump may include an annular ring. In some embodiments, the first bump may be disposed between the notch and the proximal end of the introducer needle. In some embodiments, the second bump may be disposed between the notch and the proximal end of the introducer needle and distal to the first bump. In some embodiments, the catheter may include a peripheral intravenous catheter. In some embodiments, the introducer needle may be configured to extend through the peripheral intravenous catheter.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
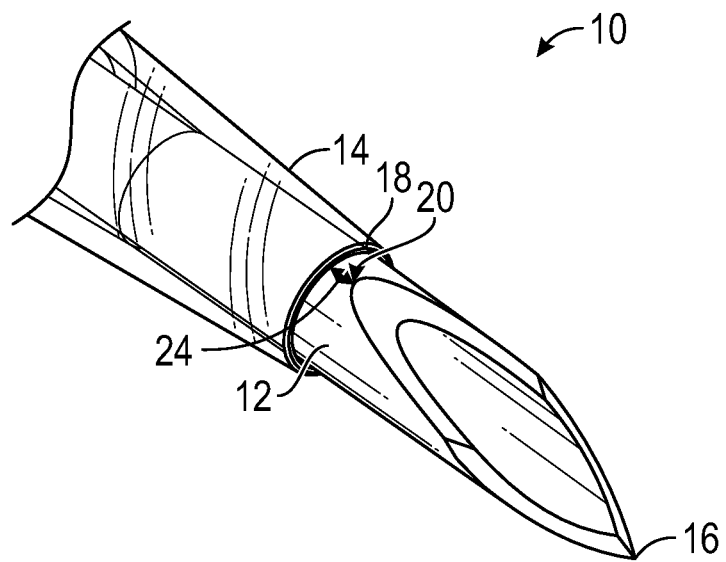
FIG. 1A is an enlarged view of a distal end of a prior art catheter system prior to insertion into a patient.

Referring now to FIG. 1A, a distal end 10 of a prior art catheter system is illustrated prior to insertion into a patient. Prior to insertion into the patient and during manufacture and assembly of the prior art catheter assembly, an introducer needle 12 may be inserted through a catheter 14 such that a sharp distal tip 16 of the introducer needle 12 is distal to a distal end 18 of the catheter 14. The introducer needle 12 extending beyond the distal end 18 of the catheter 14 may facilitate piercing of skin and vasculature of a patient and insertion of the prior art catheter system into the vasculature. A distance between the distal end 18 of the catheter 14 and a proximal end 20 of a bevel 22 of the introducer needle 12 in an assembly condition is called a lie distance 24.

Figure 1B:
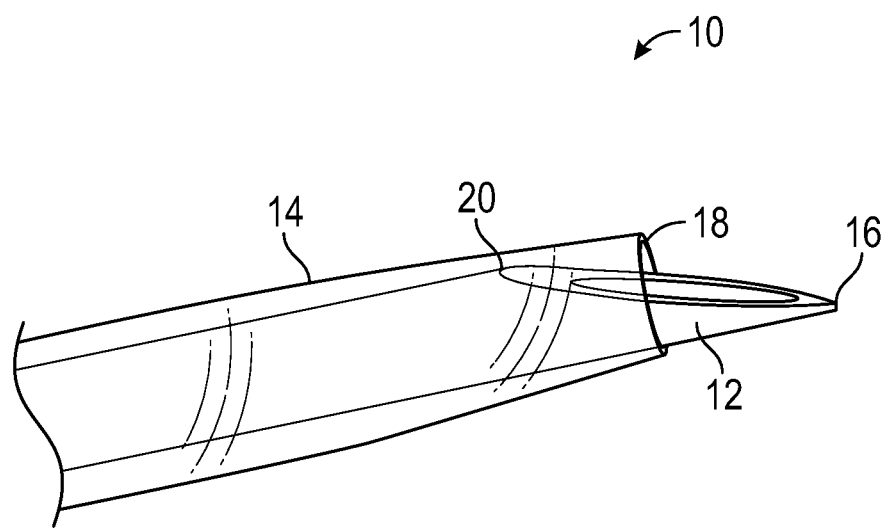
FIG. 1B is an enlarged view of the distal end of the prior art catheter system during insertion into the patient.

Referring now to FIG. 1B, in some instances, during insertion of the prior art catheter system through skin of the patient and into the vasculature, the clinician may accidentally distally advance the catheter 14 beyond the proximal end 20 of the bevel 22 or may accidentally proximally withdraw the introducer needle 44, reducing or eliminating the lie distance 24. This reduces insertion success, results in peel back of the catheter 14, and is painful to the patient.

Figure 2A:
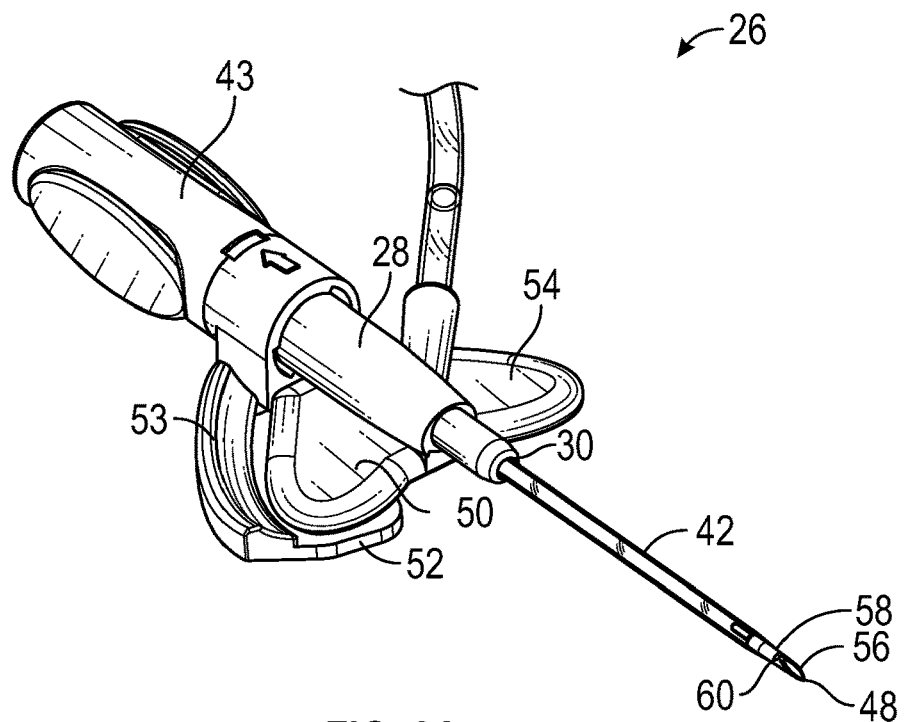
FIG. 2A is an upper perspective view of a catheter system, according to some embodiments.
Figure 2B:
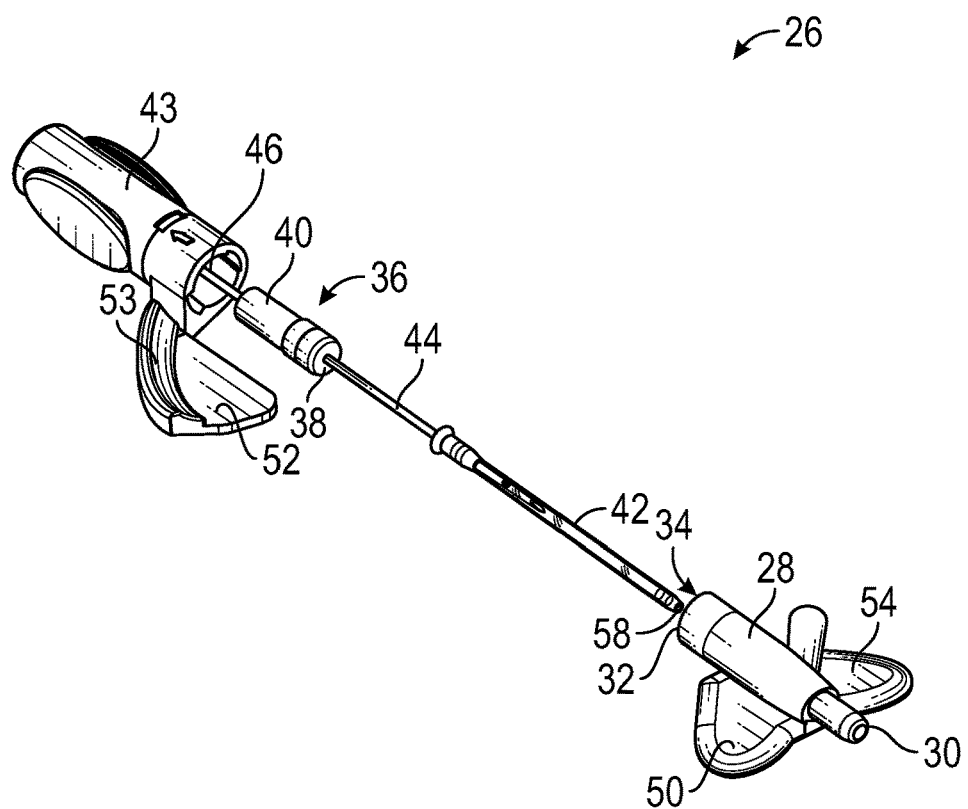
FIG. 2B is a partially exploded view of the catheter system of FIG. 2A, according to some embodiments.

Referring now to FIGS. 2A-2B, in some embodiments, a catheter system 26 may include a catheter adapter 28, which may include a distal end 30, a proximal end 32, and a lumen 34 extending through the distal end 30 of the catheter adapter 28 and the proximal end 32 of the catheter adapter 28. In some embodiments, the catheter system 26 may be similar or identical to the prior art catheter system discussed with respect to FIG. 1 in terms of one or more features or operation. In some embodiments, the catheter system 26 may include a septum assembly 36 disposed within the lumen 34 of the catheter adapter 28. In some embodiments, the septum assembly 36 may include a septum 38 and/or a septum canister 40.

In some embodiments, the catheter system 26 may include a catheter 42 extending from the distal end 30 of the catheter adapter 28. In some embodiments, the catheter system 26 may include a needle hub 43 coupled to the proximal end 32 of the catheter adapter 28. In some embodiments, the catheter system 26 may include an introducer needle 44, which may include a proximal end 46 and a sharp distal tip 48. In some embodiments, the proximal end 46 of the introducer needle 44 may be secured within the needle hub 43.

In some embodiments, a catheter assembly may include a wing 50, which may extend outwardly from the catheter adapter 28. In some embodiments, the catheter assembly may also include the catheter adapter 28 and the catheter 42, and a needle assembly may include the needle hub 43 and the introducer needle 44. In some embodiments, the needle assembly may include a paddle hub 52 extending outwardly from the needle hub 43. In some embodiments, the paddle hub 52 may include a lip 53 configured to abut the wing 50 and prevent proximal movement of the wing 50 with respect to the paddle hub 52. In some embodiments, the wing 50 may be configured to slide distally with respect to the paddle hub 52. In some embodiments, another wing 54 may extend outwardly from the catheter adapter 28 in a direction opposite the wing 50.

In some embodiments, the sharp distal tip 48 of the introducer needle 44 may include a bevel 56. In some instances, during insertion of the catheter 42 through the skin and into the vasculature of the patient, there may be a tendency for a distal end 58 of the catheter 42 to be disposed distal to a proximal end 60 of the bevel 56. This may occur in response to the clinician accidentally distally advancing the catheter 14 beyond the proximal end 20 of the bevel 22 or proximally withdrawing the introducer needle 44, reducing or eliminating a lie distance 62 (see FIG. 2E). There may be a tendency for the lie distance 62 to reduced or eliminated because of low friction between the wing 50 and the paddle hub 52, an assembly condition having a reduced lie distance, or the clinician holding the wing 50 and the paddle hub 52 together during insertion of the catheter 42 (resulting in a premature "money grip" advancement). Elimination of the lie distance 62 is undesirable during initial insertion through the skin and a wall of the vasculature, because it may reduce insertion success, result in peel back of the catheter 42, and may be painful to the patient.

Figure 2C:
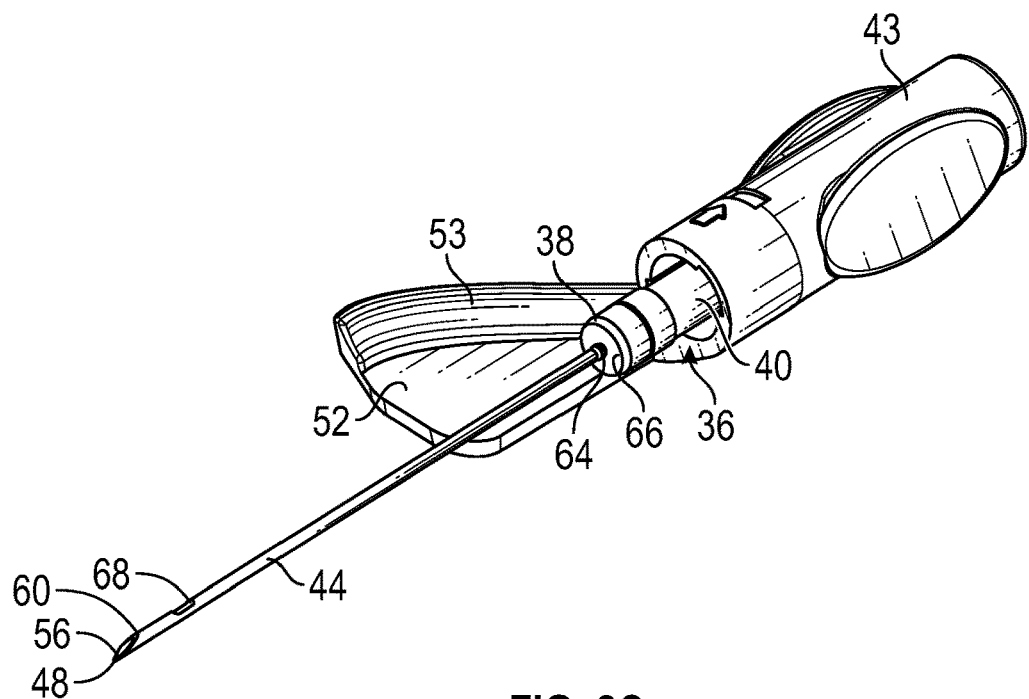
FIG. 2C is an upper perspective view of an example needle assembly and example septum assembly of the catheter system of FIG. 2A, according to some embodiments.
Figure 2D:
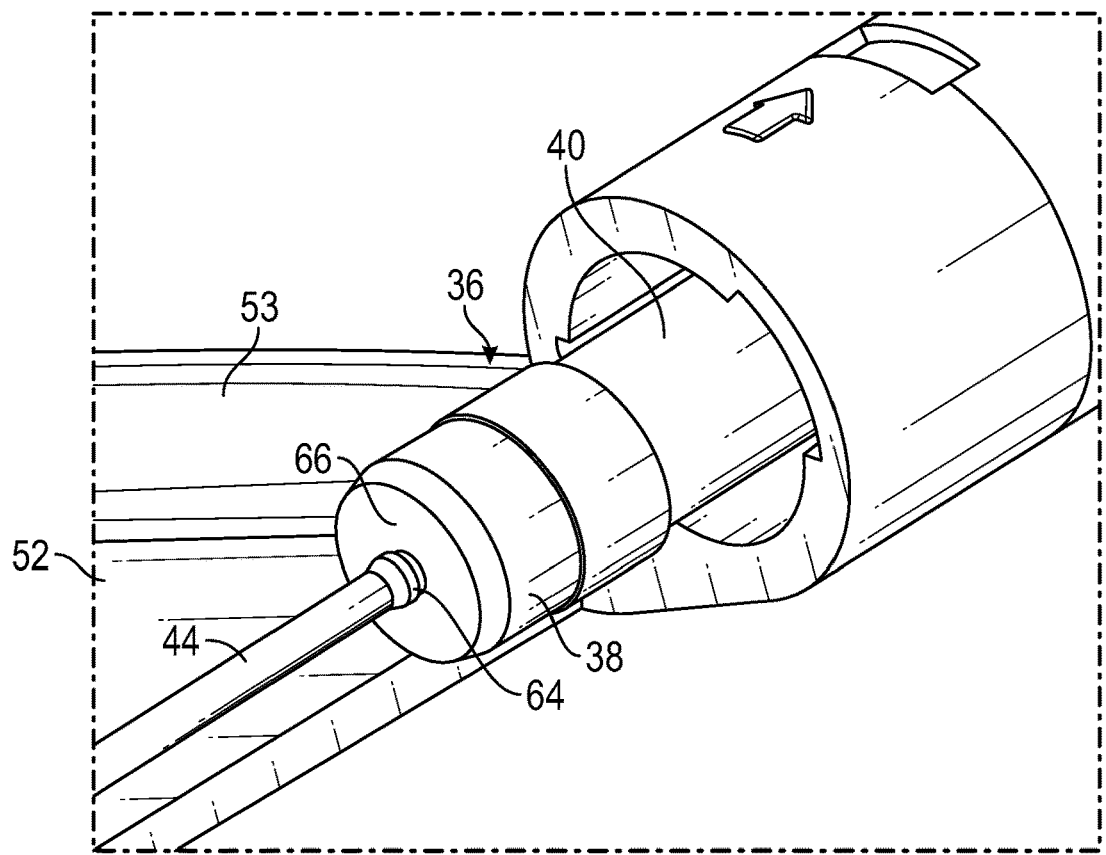
FIG. 2D is an enlarged upper perspective view of the needle assembly and the septum assembly of FIG. 2A, according to some embodiments.
Figure 2E:
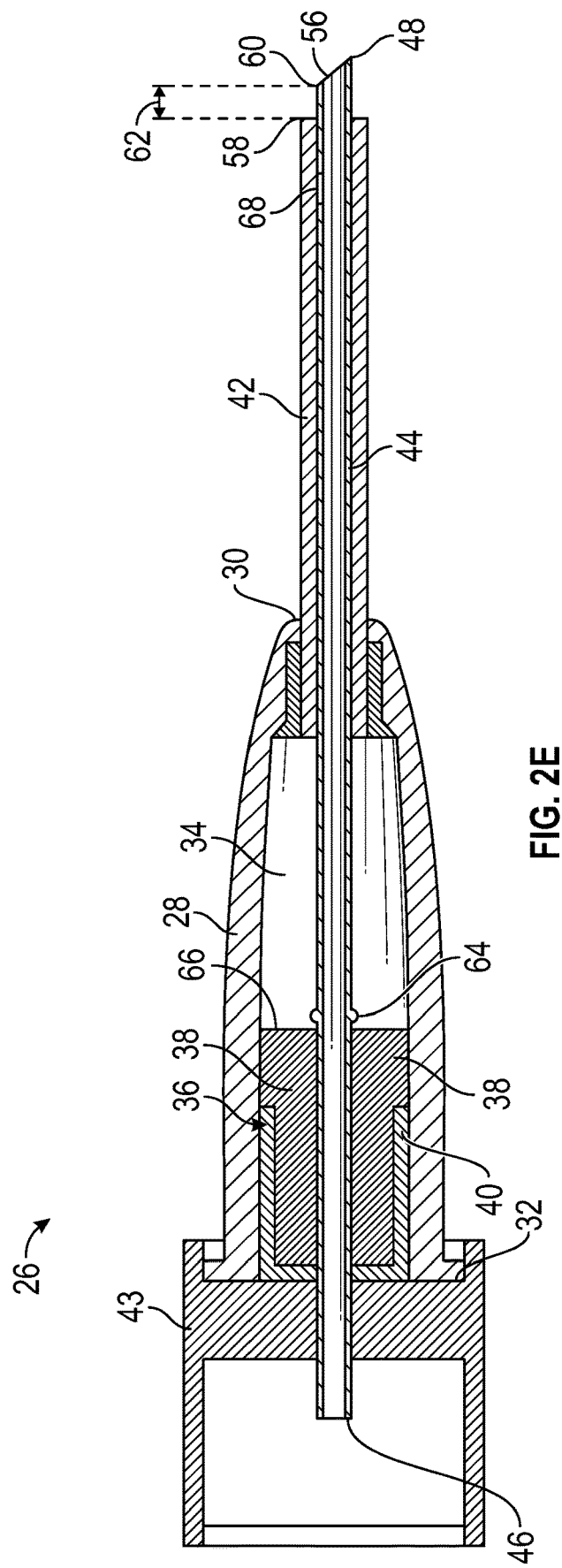
FIG. 2E is a cross-sectional view of the catheter system of FIG. 2A, according to some embodiments.

In some embodiments, the catheter system 26 may be configured to provide the clinician with a tactile indication to prevent the distal end 58 of the catheter 42 from being disposed distal to a proximal end 60 of the bevel 56. Referring now to FIGS. 2C-2E, in some embodiments, the introducer needle 44 may include a bump 64 disposed between the proximal end 46 and the sharp distal tip 48. In some embodiments, the bump 64 may provide the clinician with the tactile indication to prevent the distal end 58 of the catheter 42 from being disposed distal to a proximal end 60 of the bevel 56. In further detail, in some embodiments, the clinician may sense the bump 64 contacting the septum assembly 36, which may indicate to the clinician to be careful not to withdraw the introducer needle 44 any further (proximally) with respect to the catheter 42 and/or not to advance the catheter 42 any further (distally) with respect to the introducer needle 44. In some embodiments, the bump 64 may not only provide the tactile indication but may also increase a force necessary for the clinician to position the distal end 58 of the catheter 42 distal to a proximal end 60 of the bevel 56, reducing a risk of eliminating the lie distance 62.

In some embodiments, in response to the bump 64 contacting the septum assembly 36, the sharp distal tip 48 of the introducer needle 44 may be disposed distal to the distal end 58 of the catheter 42. Thus, the sharp distal tip 48 is still exposed from the catheter 42, facilitating insertion success.

A distance between the distal end 58 of the catheter 42 and a proximal end 60 of the bevel 56 in an assembly condition (illustrated, for example, in FIGS. 2A-2F) is called the lie distance 62. The catheter system 26 may be ready for insertion into the patient in the assembly condition. In some embodiments, a distance between the bump 64 and the septum assembly 36 (in the assembly condition) may be less than or equal to the lie distance 62 between the distal end 58 of the catheter 42 and a proximal end 60 of the bevel 56. Thus, the bump 64 may discourage movement between the catheter 42 and the introducer needle 44 that is greater than or equal to the lie distance 62.

In some embodiments, the septum assembly 36 may include a distal end 66. In some embodiments, the distal end 66 may include the septum 38, which may be a low-drag septum and/or constructed of a flexible material. In some embodiments, the distal end 66 may include the septum canister 40.

In some embodiments, the septum 38 may include any suitable septum. In some embodiments, the septum canister 40 may include any suitable septum canister. In some embodiments, the catheter system 26 may include or correspond to any suitable catheter assembly, such as, for example, the BD NEXIVA™ Closed IV Catheter system, the BD CATHENA™ Catheter system, the BD VENFLON™ Pro Safety Shielded IV Catheter system, or another suitable catheter system.

In some embodiments, the bump 64 may be distal to and spaced apart from the septum assembly 36, as illustrated, for example in FIGS. 2D-2E. In some embodiments, the bump 64 may be no more than 2 mm from the septum assembly. In some embodiments, the introducer needle 44 may be hooded after initial insertion through the skin and the wall of the vasculature. Hooding the introducer needle 44 may reduce a risk of injuring an inner surface of the vasculature as the catheter 42 is advanced and secured further within the vasculature. When the introducer needle 44 is hooded, the introducer needle 44 is slightly withdrawn with respect to the catheter 42, resulting in the bevel 56 being at least partially disposed within the catheter 42. In some embodiments, the bump 64 may be placed about 2 mm or no more than 2 mm from the septum canister 40 (in the assembly condition) to facilitate hooding the sharp distal tip 48 after initial insertion through the skin and the wall of the vasculature.

In some embodiments, the bump 64 may be more than 2 mm from the septum assembly 36 (in the assembly condition). In some embodiments, the bump 64 may be less than 2 mm from the septum assembly 36 (in the assembly condition). In some embodiments, the septum assembly 36 may include the distal end 66, and the bump 64 may be in contact with the distal end 66 of the septum assembly 36 (in the assembly condition). In some embodiments, the bump 64 may be placed between 2-3 mm from the septum assembly 36 (in the assembly condition).

Figure 2F:
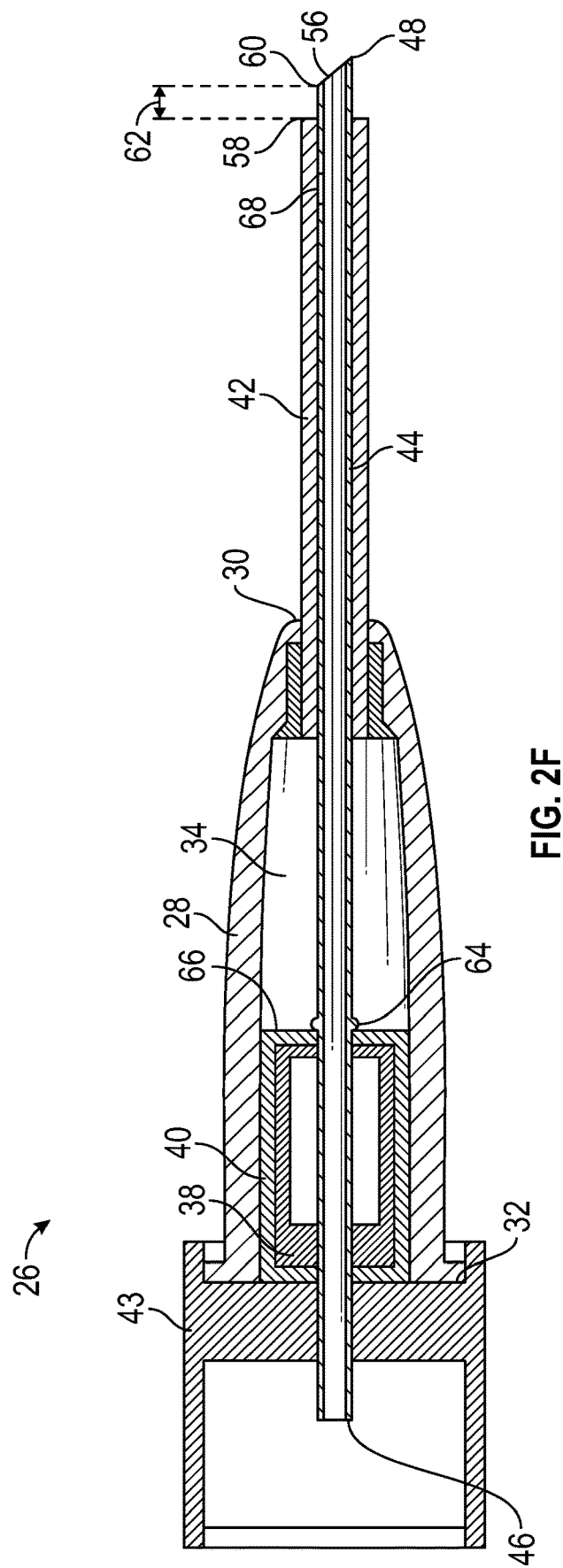
FIG. 2F is a cross-sectional view of the catheter system of FIG. 2A, according to some embodiments.

Referring now to FIG. 2F, in some embodiments, the distal end 66 may include the septum 38, which may be a low-drag septum and/or constructed of a flexible material. In some embodiments, the distal end 66 may include the septum canister 40, as illustrated, for example, in FIG. 2F. In some embodiments, the septum canister 40 may be constructed of a rigid or semi-rigid material, which may provide a greater force to overcome and/or a greater tactile indication in response to contact with the bump 64. In some embodiments, the septum canister 40 may be constructed of metal.

In some embodiments, the introducer needle 44 may include a notch 68 distal to the bump 64. In some embodiments, the notch 68 may be in fluid communication with a lumen of the introducer needle 44 and may facilitate observation of flashback within the catheter 42.

Referring now to FIG. 2F, in some embodiments, the proximal end 66 may include the septum 38, which may be a low-drag septum and/or constructed of a flexible material. In some embodiments, the proximal end 66 may include the septum canister 40, as illustrated, for example, in FIG. 2F. In some embodiments, the septum canister 40 may be constructed of a rigid or semi-rigid material, which may provide a greater force to overcome and/or a greater tactile indication in response to contact with the bump 64. In some embodiments, the septum canister 40 may be constructed of metal.

In some embodiments, the bump 64 may be in contact with the distal end 66 of the septum assembly 36 (in the assembly condition), which may reduce a risk of any movement between the introducer needle 44 and the catheter and facilitate maintenance of the lie distance 62. Embodiments of the present disclosure may be combined. For example, FIG. 2E may include the septum 38 that is low-drag and/or the proximal end 66 that includes the septum canister 40.

Figure 3A:
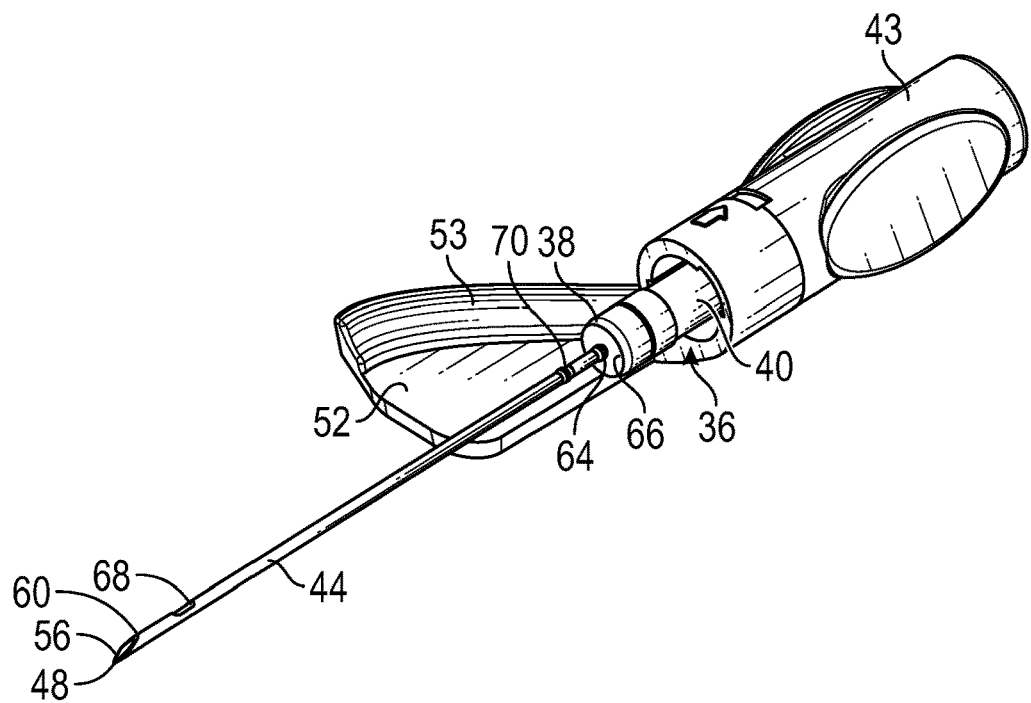
FIG. 3A is an upper perspective view of an example needle assembly and the septum assembly of FIG. 2A, according to some embodiments.
Figure 3B:
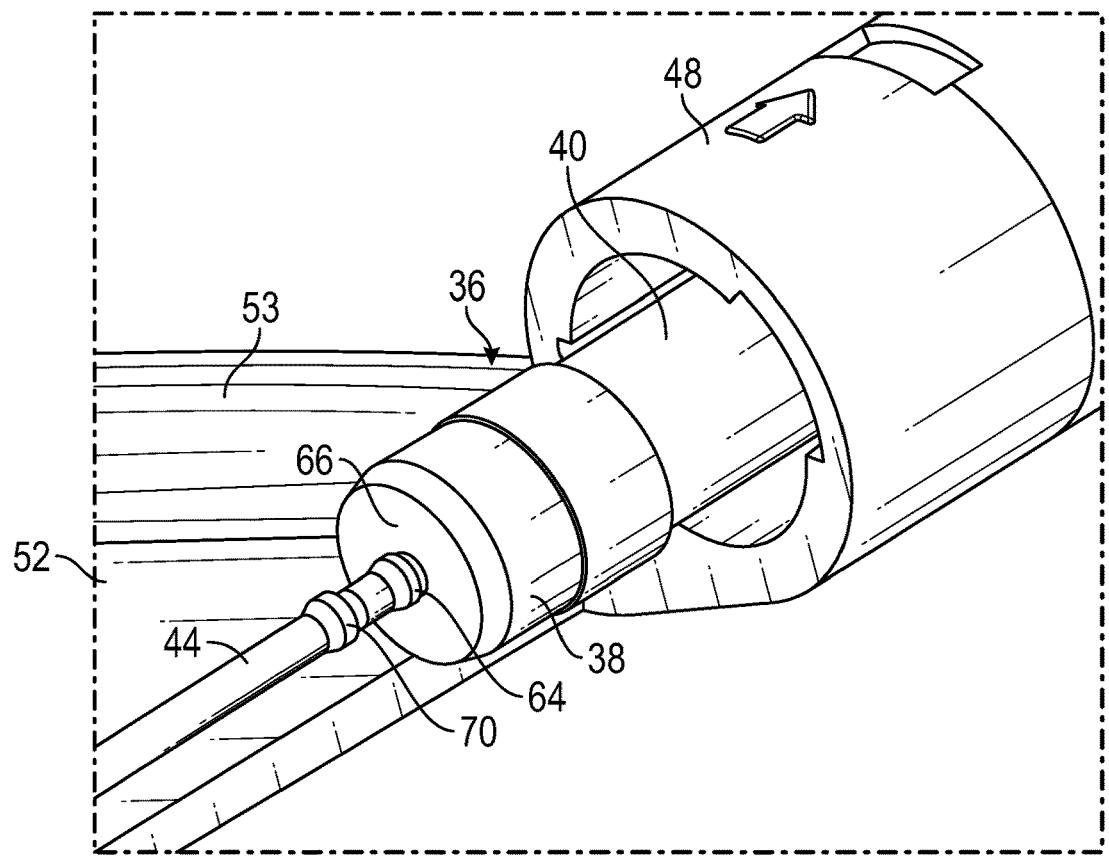
FIG. 3B is an enlarged upper perspective view of the needle assembly and the septum assembly of FIG. 3A, according to some embodiments.
Figure 3C:
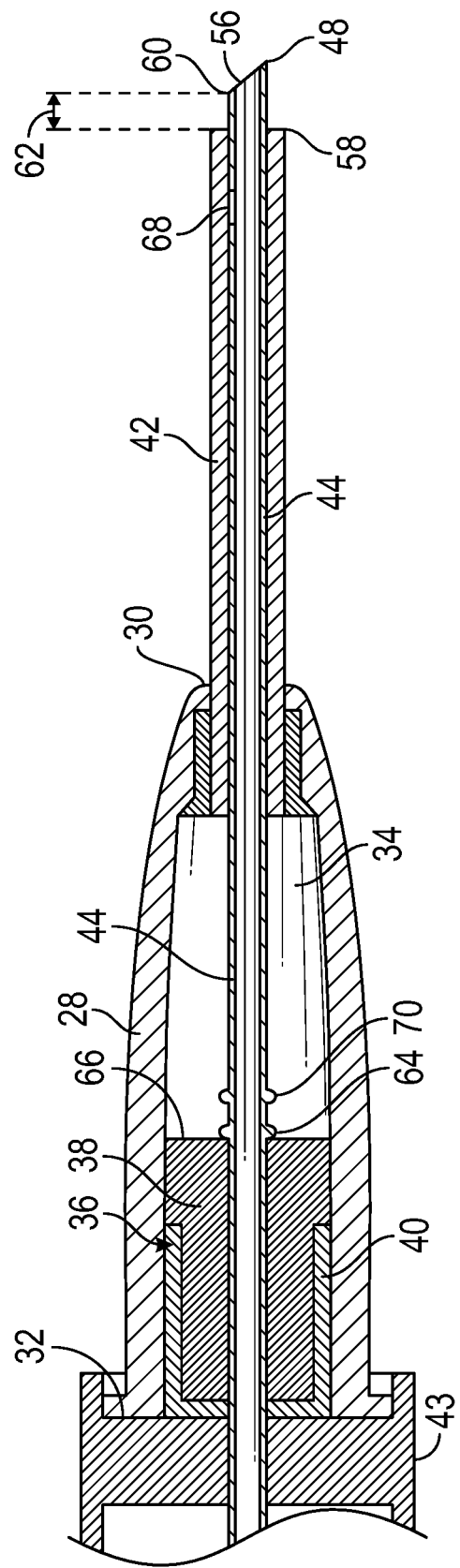
FIG. 3C is a cross-sectional view of another example catheter system that includes the needle assembly and the septum assembly of FIG. 3A, according to some embodiments.

Referring now to FIGS. 3A-3C, in some embodiments, the bump 64 is a first bump, and the introducer needle 44 may include a second bump 70 distal to the first bump. FIGS. 3A-3C illustrate the catheter system 26 in the assembly condition and ready for insertion into the patient, according to some embodiments. In some embodiments, the second bump 70 may provide an additional tactile indication to prevent the distal end 58 of the catheter 42 from being disposed distal to a proximal end 60 of the bevel 56. In some embodiments, the second bump 70 may also provide a greater force for the clinician to overcome in order for the distal end 58 of the catheter 42 to be positioned distal to a proximal end 60 of the bevel 56, a position that may not be desired.

In some embodiments, in response to the second bump 70 contacting the septum assembly 36, the sharp distal tip 48 of the introducer needle 44 may be disposed distal to the distal end 58 of the catheter 42. In some embodiments, the sharp distal tip 48 of the introducer needle 44 may include the bevel 56, and a distance between the second bump 70 and the septum assembly 36 may be less than or equal to the lie distance 62 between the distal end 58 of the catheter 42 and the proximal end 60 of the bevel 56 of the introducer needle 44.

In some embodiments, the septum assembly 36 may include the distal end 66. In some embodiments, the second bump 70 may be in contact (in the assembly condition) with the distal end 66 of the septum assembly 36, which may include the septum 38 and/or the septum canister 40. In some embodiments, this may reduce a risk of any movement between the introducer needle 44 and the catheter and facilitate maintenance of the lie distance 62.

In some embodiments, the second bump 70 may be distal to and spaced apart from the septum assembly 36 (in the assembly condition). In some embodiments, the second bump 70 may be no more than 2 mm from the septum assembly 36 (in the assembly condition). In some embodiments, the second bump 70 may be placed about 2 mm or no more than 2 mm from the septum assembly 36 (in the assembly condition) to facilitate hooding the sharp distal tip 48 after initial insertion through the skin and the wall of the vasculature. In some embodiments, the second bump 70 may be more than 2 mm from the septum assembly 36 (in the assembly condition). In some embodiments, the second bump 70 may be less than 2 mm from the septum assembly 36 (in the assembly condition). In some embodiments, the second bump 70 may be placed between 2-3 mm from the septum assembly 36 (in the assembly condition).

In some embodiments, the first bump and/or the second bump 70 may include an annular ring. In some embodiments, the first bump may be disposed between the notch 68 and the proximal end 46 of the introducer needle 44 and/or the second bump 70 may be disposed between the notch 68 and the proximal end 46 of the introducer needle 44 and proximal to the first bump. In some embodiments, the catheter 42 may include a peripheral intravenous catheter, a peripherally inserted central catheter, a midline catheter, or another suitable catheter. In some embodiments, the introducer needle 44 may be configured to extend through the peripheral intravenous catheter in the assembly condition.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
   a catheter adapter, comprising a distal end, a proximal end, and a lumen extending through the distal end of the catheter adapter and the proximal end of the catheter adapter;
   a septum assembly disposed within the lumen of the catheter adapter, wherein the septum assembly comprises a septum and a septum canister, wherein the septum assembly comprises a distal end;
   a catheter extending from the distal end of the catheter adapter;
   a needle hub coupled to the proximal end of the catheter adapter; and
   an introducer needle comprising a proximal end, a sharp distal tip, and a bump disposed between the proximal end and the sharp distal tip, wherein the proximal end of the introducer needle is secured within the needle hub, wherein the bump first contacts the distal end of the septum assembly when the introducer needle is proximally withdrawn from an assembly condition, wherein in response to the bump contacting the distal end of the septum assembly, the sharp distal tip of the introducer needle is disposed distal to a distal end of the catheter.

2. The catheter system of claim 1, wherein the sharp distal tip of the introducer needle comprises a bevel, wherein in the assembly condition, the bump is distal to the septum assembly and a distance between the bump and the septum assembly is less than or equal to a lie distance between the distal end of the catheter and a proximal end of the bevel of the introducer needle.

3. The catheter system of claim 1, wherein the bump is in contact with the distal end of the septum assembly in the assembly condition.

4. The catheter system of claim 1, wherein the bump is distal to and spaced apart from the septum assembly in the assembly condition.

5. The catheter system of claim 4, wherein the bump is no more than 2 mm from the septum assembly in the assembly condition.

6. The catheter system of claim 1, wherein the catheter system further comprises a wing extending outwardly from the catheter adapter, wherein the catheter system further comprises a paddle hub extending outwardly from the needle hub, wherein the paddle hub comprises a lip configured to abut the wing and prevent proximal movement of the wing with respect to the paddle hub, wherein the wing is configured to slide distally with respect to the paddle hub.

7. The catheter system of claim 1, wherein the bump is a first bump, wherein the introducer needle comprises a second bump distal to the first bump.

8. The catheter system of claim 7, wherein in response to the second bump contacting the septum assembly, the sharp distal tip of the introducer needle is disposed distal to the distal end of the catheter.

9. The catheter system of claim 7, wherein the sharp distal tip of the introducer needle comprises a bevel, wherein in the assembly condition, the second bump is distal to the septum assembly and a distance between the second bump and the septum assembly is less than or equal to a lie distance between the distal end of the catheter and a proximal end of the bevel of the introducer needle.

10. The catheter system of claim 7, wherein the first bump is in contact with the distal end of the septum assembly.

11. The catheter system of claim 7, wherein in the assembly condition, the first bump is distal to and spaced apart from the septum assembly.

12. The catheter system of claim 7, wherein the second bump is no more than 2 mm from the septum assembly in the assembly condition.

13. The catheter system of claim 7, wherein the first bump and the second bump each comprise an annular ring.

14. The catheter system of claim 1, wherein the introducer needle comprises a notch distal to the bump.

15. The catheter system of claim 1, wherein the catheter is a peripheral intravenous catheter.

16. The catheter system of claim 1, wherein the bump comprises an annular ring.

17. The catheter system of claim 1, wherein the distal end of the septum assembly comprises the septum canister.

18. The catheter system of claim 1, wherein the distal end of the septum assembly comprises the septum.

* * * * *